(12) United States Patent
Gilmore et al.

(10) Patent No.: US 8,478,555 B2
(45) Date of Patent: Jul. 2, 2013

(54) SYSTEM AND METHODS OF IMPROVED TOMOGRAPHY IMAGING

(75) Inventors: Colin Gilmore, Winnipeg (CA); Joe LoVetri, Winnipeg (CA)

(73) Assignee: University of Manitoba, Winnipeg (CA)

( * ) Notice: Subject to any disclaimer, the term of this patent is extended or adjusted under 35 U.S.C. 154(b) by 473 days.

(21) Appl. No.: 12/741,310

(22) PCT Filed: Nov. 21, 2008

(86) PCT No.: PCT/IB2008/003930
§ 371 (c)(1),
(2), (4) Date: Sep. 10, 2010

(87) PCT Pub. No.: WO2009/066186
PCT Pub. Date: May 28, 2009

(65) Prior Publication Data
US 2011/0046907 A1     Feb. 24, 2011

Related U.S. Application Data

(60) Provisional application No. 61/003,891, filed on Nov. 21, 2007.

(51) Int. Cl.
*G06F 15/00*     (2006.01)
(52) U.S. Cl.
USPC .................. 702/85; 250/363.02; 250/363.04; 250/370.08; 600/425

(58) Field of Classification Search
USPC ..... 702/85; 324/307, 309, 315, 637; 600/410, 600/430, 425; 250/363.02–363.05, 370.08
See application file for complete search history.

(56) References Cited

U.S. PATENT DOCUMENTS 6,332,087 B1     12/2001     Svenson et al.
2006/0012367 A1   1/2006     Meaney et al.

OTHER PUBLICATIONS

Arunachalam et al., "Microwave Imaging of Penetrable Scatterers Using Deformable Mirror", IEEE Transactions on Magnetics, Apr. 2007, pp. 1805-1808, vol. 43, No. 4.
Semenov et al., "Microwave-Tomographic Imaging of the High Dielectric-Contrast Objects Using Different Image-Reconstruction Approaches", IEEE Transactions on Microwave Theory and Techniques, Jul. 2005, pp. 2284-2294, vol. 53, No. 7.

*Primary Examiner* — Jonathan C Teixeira Moffat
*Assistant Examiner* — Hien Vo
(74) *Attorney, Agent, or Firm* — Valauskas Corder LLC

(57) ABSTRACT

The present invention is a system and methods of improved tomography imaging such as microwave tomography (MWT). An improved inversion technique surrounds the imaging region with an electrically conducting surface to create field distortions producing an improved tomographic image. The improved inversion technique of the present invention creates a new physical situation for proposed imaging systems.

9 Claims, 16 Drawing Sheets

SYSTEM AND METHODS OF IMPROVED TOMOGRAPHY IMAGING

FIELD OF THE INVENTION

The present invention relates generally to tomography imaging. More particularly, the present invention relates to an improved inversion technique that surrounds the imaging region with an electrically conducting surface to produce an improved tomographic image.

BACKGROUND OF THE INVENTION

The present invention is discussed in the following largely with reference to the medical industry, but the present invention is applicable to a variety of contexts and environments, each of which may utilize or benefit from an improved tomographic imaging system, for example, archaeology, biology, geophysics, materials science, electron microscopy, security scanning, industrial nondestructive testing, astronomy and others.

Tomography is imaging by sections or sectioning to convey internal structures of a solid object, for example the human body or the earth. Slices of the object are viewed without physically cutting the object. A device used in tomography is called a tomograph. A tomograph generates a tomogram, or image.

The image, or tomogram, can be achieved by tomography applications such as acoustic tomography, atom probe tomography (APT), computed tomography (CT), confocal laser scanning microscopy (LSCM), cryo-electron tomography (Cryo-ET), electrical capacitance tomography (ECT), electrical resistance tomography (ERT), electrical impedance tomography (EIT), functional magnetic resonance imaging (fMRI), magnetic induction tomography (MIT), magnetic resonance imaging (MRI), formerly known as magnetic resonance tomography (MRT), neutron tomography, optical coherence tomography (OCT), optical projection tomography (OPT), process tomography (PT), positron emission tomography (PET), quantum tomography, single photon emission computed tomography (SPECT), seismic tomography, and X-ray tomography.

Electromagnetic and acoustic tomography requires the inversion of a wave equation. More modern variations of tomography involve gathering projection data from multiple directions and feeding the data into a tomographic reconstruction algorithm processed by a computer in order to create a tomographic image. The reconstruction algorithm includes an inversion technique.

Various inversion techniques for wave equations arising from electromagnetic and acoustic scattering imaging systems have been developed since the early 1980s. Scattering is a general physical process whereby some forms of radiation, such as light, sound or moving particles, for example, are forced to deviate from a straight trajectory by one or more non-uniformities in the medium through which it passes. It is the inverse problem to the direct scattering problem that determines the characteristics of an object such as its shape and internal constitution from measurement data of radiation or particles scattered from the object.

A substantial amount of research during the last decade or so has focused on a full non-linear inversion problem, or a non-linear inversion technique. These inversion techniques have matured to the point for possible use in biomedical imaging and identification, and experimental systems have already been created that show good potential for electromagnetic imaging of limbs and breast tumors.

An advantage of the full non-linear inversion technique, as opposed to a linearized technique, is that a quantitative inversion of material parameters such as conductivity and permittivity significantly improves solving the clinical identification problem, e.g., tumor or no tumor, and makes the non-linear inversion technique much more useful for biomedical applications.

Large classes of inversion techniques for wave-type equations are formulated as non-linear optimization problems which are then solved using an iterative method. Most of these methods require the use of a Green's function and, typically, these methods have been implemented using the Green's function associated with a scatterer located in an unbounded homogeneous region. However, this assumption rarely matches the physical situation for proposed imaging systems. For example, several recently proposed and implemented biomedical imaging systems utilize a matching medium, or fluid, contained in a tank made of material such as plexi-glass. The assumption of a homogenous background Green's function in the inversion technique ignores the field distortions caused by the matching medium, and leads to inversion artifacts.

An improved inversion technique that matches the physical situation for proposed imaging systems by creating field distortions needed to produce an improved tomographic image. The present invention satisfies this demand.

SUMMARY OF THE INVENTION

The present invention is a system and methods of improved tomography imaging such as microwave tomography (MWT). An improved inversion technique that surrounds the imaging region, otherwise referred to herein as image region, with an electrically conducting surface to create field distortions producing an improved tomographic image. The improved inversion technique of the present invention creates a new physical situation for proposed imaging systems.

The method for an improved tomographic imaging system according to the present invention comprises defining an image region. The image region is surrounded with an electrical conducting surface to form a shaped-boundary. Upon applying radiation to the image region, the system creates field distortions reflected by the shaped-boundary thereby producing an improved field distribution. The field distribution is accounted for in a mathematical inversion technique allowing for an improved tomographic image.

The present invention surrounds the imaging region with an electrically conducting surface to create field distortions to produce an improved tomographic image. The electrically conducting surface acts both as the container for the matching medium as well as a shield against external sources of radiation. The inclusion of the conductive surface differs from existing tomographic imaging systems, which typically have a plexi-glass or similar surface.

The field distortions are used in the inversion algorithm, via the appropriate Green's function. While the use of a conducting surface to surround the imaging region is not particular to any given inversion algorithm, the present invention is discussed herein in regard to the Contrast Source Inversion (CSI) algorithm, particularly the Multiplicative-Regularized Contrast Source Inversion (MR-CSI) algorithm. This CSI algorithm has been chosen for illustrative purposes only as it is contemplated that the present invention is applicable to any inversion algorithm. The CSI algorithm has been chosen for discussion of the present invention since it is known to be successful in solving the inverse problem for homogenous backgrounds. In addition, the CSI algorithm is suitable for a wide range of MWT problems.

As an example, results of the present invention are shown for the case where the electrically conducting surface is modeled by a Perfect Electric Conductor (PEC) in the shape of a circular cylinder. While the shape of the surface considered herein is a cylinder, any shape is contemplated for which a closed-form of the Green's function is known. The Electro-Magnetic (EM) radiation is modeled as a 2D Transverse Magnetic (2D-TM) problem. A form of the 2D-TM circular-cylinder Green's function that is easily utilized in existing electromagnetic codes is formulated. The formulated Green's function takes into account the fields reflected by the boundary formed by the electrically conducting surface. The formulated Green's function according to the present invention improves the performance of the inversion as compared to using an unbounded homogenous medium Green's function.

While the formulation discussed herein applies to a 2D scalar wave equation, the formulation is equally applicable to a 3D scalar wave equation as well as vector problems.

Several different synthetic examples are discussed herein that test the performance of the inversion technique when the PEC surface is present. Results show that, in many cases, the tomographic image is significantly improved. It is believed the improved inversion results are likely due to the increased interrogation energy deposited into the imaging region. Results are also shown herein that demonstrate the problems which may arise if the unbounded domain Green's function is used in an MWT system that utilizes a matching medium of finite extent—problems which are overcome by the inclusion of a PEC surface on the exterior of the MWT system.

The present invention and its attributes and advantages will be further understood and appreciated with reference to the detailed description below of presently contemplated embodiments, taken in conjunction with the accompanying drawings.

DETAILED DESCRIPTION OF EMBODIMENTS OF THE INVENTION

Figure 1:
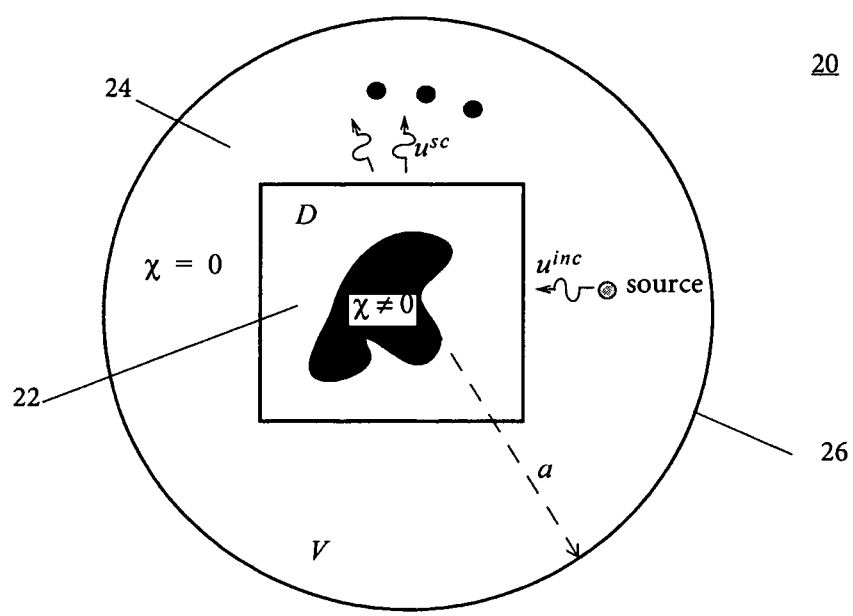
FIG. 1 illustrates an embodiment of the tomographic imaging system according to the present invention.

The present invention is an improved inversion technique that surrounds the imaging region with an electrically conducting surface, or enclosure, to create field distortions in order to produce an improved tomographic image. A schematic of the imaging region 20 is shown in FIG. 1. An unknown scatterer 22 is embedded in a matching fluid 24, which is surrounded by an electrically conductive surface 26, here a cylinder. The conductive surface 26 serves as both the enclosure for any possible matching fluid 24 and a shield from outside interference. The inclusion of the conducting enclosure considerably changes the distribution of the ElectroMagnetic (EM) energy as compared to that of an open system. Most importantly, the distorted field is taken into account in the inversion algorithm, via the appropriate Green's function discussed more fully below. Again, while the shape of the surface considered herein is a cylinder, any shape is contemplated for which a closed-form of the Green's function is known.

A 2D scalar wave equation, here a 2D Transverse Magnetic (2D-TM) problem is used with a scalar field quantity (in this case, $E_z$,) represented by the symbol u. The conducting enclosure is modeled as a Perfect Electric Conductor (PEC). The governing differential equation is the 2D scalar wave equation. A frequency domain model with an assumed $e^{j\omega t}$ time dependency is used. A series of transmitters, with positions labeled k=1 . . . K, illuminates an unknown scatterer with an incident field denoted $U^{inc}_k$. The scatterer is located entirely within a region D and is embedded in a homogenous background medium with a background permittivity of $\epsilon_b$, and a non-magnetic medium with a permeability of free-space ($\mu=\mu_0$).

The scattered field is measured outside the region D, and given by the data equation:

$$u_k^{sc}(r) = k_b^2 \int_D g(r, r')\chi(r')u_k(r')dr' \quad r \notin D, \quad (1)$$

where r is the location of the receiver, g is the background Green's function, $u_k$ is the total field of transmitter k and $u_k^{sc}$ is the scattered field.

The background wave-number is given by:

$$k_b = \omega\sqrt{\epsilon_b\mu_b} \quad (2)$$

where $\omega$ is the radial frequency. The contrast, $\chi$ is:

$$\chi(r) = \frac{\epsilon(r) - \epsilon_b}{\epsilon_b} = \frac{k_b^2}{k^2(r)} - 1 \quad (3)$$

where $k^2(r)$ and $\epsilon(r)$ are the wave-number and complex permittivity inside the scattering region, respectively. The frequency dependence of permittivities, for either the scatterer or background, is assumed to arise only from the direct current (DC) conductivity of the medium, and allowing the expression of the real and imaginary parts of the permittivity as:

$$\varepsilon = \varepsilon' + j\varepsilon'' = \varepsilon' - j\frac{\sigma}{\omega}. \quad (4)$$

For the case where the background is lossless, i.e., $\epsilon_b''=0$, the contrast may be expressed as:

$$\chi(r) = \chi' + j\chi'' = \frac{\varepsilon'(r) - \varepsilon_b}{\varepsilon_b} + j\frac{\varepsilon''(r)}{\varepsilon_b} \quad (5)$$

Thus, for lossless backgrounds, the imaginary part of the contrast is non-positive.

The fields inside the region D are modeled by the domain equation:

$$u_k(r) = u_k^{inc}(r) + k_b^2 \int_D g(r, r')\chi(r')u_k(r')dr' \quad r \in D \quad (6)$$

where now r is located inside the scattering region D. The data equation (1) and domain equation (6) form a nonlinear inverse problem for the unknown contrast, $\chi$ and the fields inside the imaging domain D.

The fundamental difference in moving from an open system to a system with a conductive enclosure is that the Green's function in the data equation (1) and domain equation (6) changes from a relatively simple Hankel function to a more complicated analytic expression for the Green's function of the enclosed problem. The closed-form expression for the modified Green's function applicable to the circular cylinder is discussed more fully below. Many of the advantages associated with the proposed imaging system derive from this change in the Green's function for the inverse problem.

As mentioned above, the Contrast Source Inversion (CSI) algorithm has been chosen for discussion of the inversion technique according to the present invention, particularly the Multiplicative-Regularized Contrast Source Inversion (MR-CSI) algorithm. Again, the present invention is not particular to a specific inversion technique and the inverse problem may be solved in a multitude of ways. Specifically, the MR-CSI algorithm is selected since it has shown extensive success as an inversion technique applied to both noisy computational and experimentally collected data. Additionally, the MR-CSI algorithm does not require any a-priori probability, although it may easily be taken into account if desired. A-priori probability is probability calculated by examining existing information. Moreover, no forward solver is required in the optimization procedure, the manual selection of a regularization parameter is not required, and it has a computational complexity of only approximately twice that of a forward solver. The MR-CSI algorithm is also suitable for wide-band simultaneous multi-frequency inversion. The formulation of the MR-CSI algorithm does not depend on the particular Green's function used, and the use of a conducting enclosure does not substantially affect the method.

The data equation is first re-written as:

$$f_k(r) = k_b^2 \int_D g(r, r')\chi(r')u_k(r')dr' \quad r \notin D, \quad (7)$$

where $f_k$ is the measured data. It is assumed that equation (7) does not hold exactly, as the data are unavoidably corrupted with noise. In symbolic notation, the data equation is now:

$$f_k = k_b^2 G^S \chi u_k \quad (8)$$

where the operator $G^S$ is defined as:

$$G^S[*] = k_b^2 \int_D g(r, r')[*]dr' \quad r \in S, \quad (9)$$

and S is a measurement surface (or set of discrete measurement points). Similarly, the domain equation is written as:

$$u_k = u_k^{inc} + G^D \chi u_k \quad (10)$$

where the operator $G^D$ is defined as:

$$G^D[*] = k_b^2 \int_D g(r, r')[*]dr' \quad r \in D. \quad (11)$$

Next, contrast sources, $w_k(r)$ are defined as:

$$w_k(r) = \chi(r)u_k(r) \quad r \in D \quad (12)$$

By multiplying both sides of the domain equation (10) with the contrast, $\chi$, and utilizing the definition of the contrast sources, it is written:

$$\chi u_k^{inc} = w_k - \chi G^D w_k \quad r \in D. \quad (13)$$

The MR-CSI algorithm formulates the inverse problem as an optimization function in two variables: the contrast, $\omega$, and the contrast sources, w. The objective function is minimized via an iterative optimization scheme. The core of the MR-CSI algorithm is the objective function:

$$F_n = F(w_{k,n}, \chi_n) = F^S(w_{k,n}) + F^D(w_{k,n}, \chi_2), \quad (14)$$

where each term on the right hand side is created by summing over the transmitter locations:

$$F^S(w_{k,n}) = \frac{\sum_k \|\rho_{k,N}\|_S^2}{\sum_k \|f_k\|_S^2} \text{ and } F^D(w_{k,n}, \chi_n) = \frac{\sum_k \|r_{k,n}\|_D^2}{\sum_k \|\chi_n u_k^{inc}\|_D^2}. \quad (15)$$

Here $\rho$ is the data error, defined as:

$$\rho_{k,n}(r) = f_k(r) - G^S w_{k,n} \quad r \in S, \quad (16)$$

and $r_{k,n}$, known as the domain, or object, error, is defined as:

$$r_{k,n}(r) = \chi_n u_{k,n} - w_{k,n} = \chi G^D w_k + \chi u_k^{inc} - w_{k,n} \quad r \in D \quad (17)$$

The index n=1 . . . N represents the iteration number. The normalization terms in both $F^S$ and $F^D$ of equation (15) are utilized to balance between the two terms in the overall objective function.

The inclusion of the domain equation inside the objective function obviates the need for a separate forward solver. The minimization over both unknowns $\chi$ and $w_k$ is performed sequentially by taking alternating steps of the conjugate gradient minimization algorithm on each unknown. Closed-form expressions used in this minimization algorithm are available, which significantly increases computational efficiency.

Multiplicative Regularization (MR), which is based on minimizing the total variation of the contrast, enhances the CSI algorithm. MR significantly improves the performance of the algorithm in noisy environments and eliminates the need for a user-selected regularization parameter, such as that required in Tikhonov regularization. The MR-CSI objective function becomes:

$$C = F_{TV}(\chi_n)F_n(w_{k,n}, \chi_n) \quad (18)$$

where:

$$F_{TV}(\chi_n) = \frac{1}{A}\int_D \frac{|\nabla \chi_n(r)|^2 + \delta_{n-1}^2}{|\nabla \chi_{n-1}(r)|^2 + \delta_{n-1}^2}dr \quad (19)$$

where A is the area of the imaging region D, $\delta_{n-1}^2 = F_{n-1}^D \Delta^{-2}$ and $\Delta$ is the length of a side of single cell in the discretized domain, in other words $\Delta^{-2}$ represents the reciprocal of the area of a single cell area of the domain D. For example, on a rectangular grid $\Delta^{-2} = 1/(\Delta x \Delta y)$.

In order to implement both a forward solver to generate synthetic data, and the actual MR-CSI inversion algorithm, an appropriate closed-form of the Green's function for the enclosed homogenous region is required. To get this appropriate closed-form of the Green's function, the solution is sought for the scalar wave equation when the boundary condition is a circular PEC cylinder. The surface of the PEC cylinder is denoted by S, and the region enclosed by the cylinder is denoted by V. The governing differential equation, or the wave equation, is given by:

$$\nabla^2 u(r)+k(r)^2 u(r)=-F(r) r \in V \qquad (20)$$

where u is the scalar field quantity of interest, k is the wave number that may depend on position, F is a source term, and r represents position. The field quantity u must also satisfy the boundary condition:

$$u(r;\omega)=0 r \in S \qquad (21)$$

on the surrounding PEC surface.

The Green's function for a homogenous medium satisfies the equation:

$$\nabla^2 g(r,r')+k^2 g(r,r')=-\delta(r-r') r \in V. \qquad (22)$$

Different Green's functions can be chosen based on the selection of the shape of the conducting boundary as well as the boundary conditions associated with equation (22). It is contemplated that the shape of the conducting boundary as well as the boundary conditions may be selected to best suit a particular problem. By considering Green's second identity:

$$\int_V (\phi \nabla^2 \psi - \psi \nabla^2 \phi) dV = \oint_S \left(\phi \frac{\partial \psi}{\partial n} - \psi \frac{\partial \phi}{\partial n}\right) dS, \qquad (23)$$

and noting that:

$$\nabla^2 u(r)=-F(r)-k^2 u(r)$$

$$\nabla^2 g(r,r')=-\delta(r-r')-k^2 g(r,r') \qquad (24)$$

it can be written:

$$u(r) = \int_V g(r,r') F(r') dr' + \oint_S \left(u \frac{\partial g}{\partial n} - g \frac{\partial u}{\partial n}\right) dS. \qquad (25)$$

If this were a free-space problem, the surface integral can be eliminated by selecting g=0 on S and requiring that g satisfies the Sommerfeld radiation condition. However, these conditions cannot be utilized with a PEC surface. Thus, the modified Green's function is utilized. A function, p (r, r') is introduced that satisfies the homogenous scalar Helmholtz equation:

$$\nabla^2 p(r,r')+k^2 p(r,r')=0 r \in V, \qquad (26)$$

and the modified Green's function is defined as:

$$g(r,r')=g_{fs}(r,r')+p(r,r'), \qquad (27)$$

where $g_{fs}$ (r, r') is the free-space Green's function in other words, the usual Green's function in the absence of the PEC surface. It may be noted that the addition of the function p makes no contribution to the right hand side of (22). Assuming that g satisfies the PEC boundary condition, then:

$$p(r,r')=-g_{fs}(r,r') r \in S, \qquad (28)$$

and thus the differential equation for the function p becomes:

$$\nabla^2 p(r,r')+k^2 p(r,r')=0 r \in V$$

$$p(r,r')=-g_{fs}(r,r') r \in S \qquad (29)$$

With this construction, and the assumption that the derivative of the Green's function is finite on the surface S, the surface integral in equation (25) is eliminated, thus:

$$u(r) = \int_\gamma g(r,r') F(r') dr'. \qquad (30)$$

In order to utilize the Green's function as derived above, an expression for the function p must be found. The homogenous differential equation of equation (29) may be solved via the introduction of a cylindrical coordinate system for r, (r, θ), centered at the origin and using separation of variables. The eigenfunction expansion of p is given by (see Appendix for the full derivation):

$$p(r, \theta, r') = \qquad (31)$$

$$\frac{A_0}{\sqrt{2\pi}} J_0(kr) + \sum_{n=1}^{\infty} \left(A_n J_n(kr) \frac{\cos(n\theta)}{\sqrt{\pi}} + B_n J_n(kr) \frac{\sin(n\theta)}{\sqrt{\pi}}\right).$$

where $J_n$, is the '$n^{th}$' order Bessel function of the first kind, and the coefficients $A_n$ and $B_n$, are given by:

$$A_n(r;r') = \frac{-1}{\sqrt{\pi} J_n(ka)} \int_{-\pi}^{\pi} g_{fs}(a, \theta, r') \cos(n\theta) d\theta \text{ and} \qquad (32)$$

$$B_n(r, r') = \frac{-1}{\sqrt{\pi} J_n(ka)} \int_{-\pi}^{\pi} g_{fs}(a, 0.r') \sin(n\theta) d\theta,$$

where α is the radius of the cylinder. Here:

$$g_{fs}(r, r') = \frac{1}{4j} H_0^{(2)}(k|r-r'|). \qquad (33)$$

where $H_0^{(2)}$ is the zero-th order Hankel function of the second kind, which is the 2D homogenous space Green's function corresponding to the use of $e^{j\omega t}$ time dependency.

Closed-form expressions for $A_n$ and $B_n$ may be derived (see Appendix), and are given by:

$$A_n = \frac{-\pi}{4j\sqrt{\pi} J_n(ka)} [J_n(k|r'|) e^{-jn\phi'} H_n^{(2)}(k|r|) + \qquad (34)$$

$$J_{-n}(k|r'|) e^{jn\phi'} H_{-n}^{(2)}(k|r|)]$$

and:

$$B_n = \qquad (35)$$

$$\frac{-\pi}{4j\sqrt{\pi} J_n(ka)} [J_m(k|r'|) e^{-jn\phi'} H_n^{(2)}(k|r|) + J_{-n}(k|r'|) e^{jn\phi'} H_{-n}^{(2)}(k|r|)],$$

where $H_m^{(2)}$ is the $m^{th}$ order Hankel function of the second kind, and Φ' is the associated with the position vector r'. These closed-form expressions significantly reduce computation time for the Green's function.

Figure 2A:
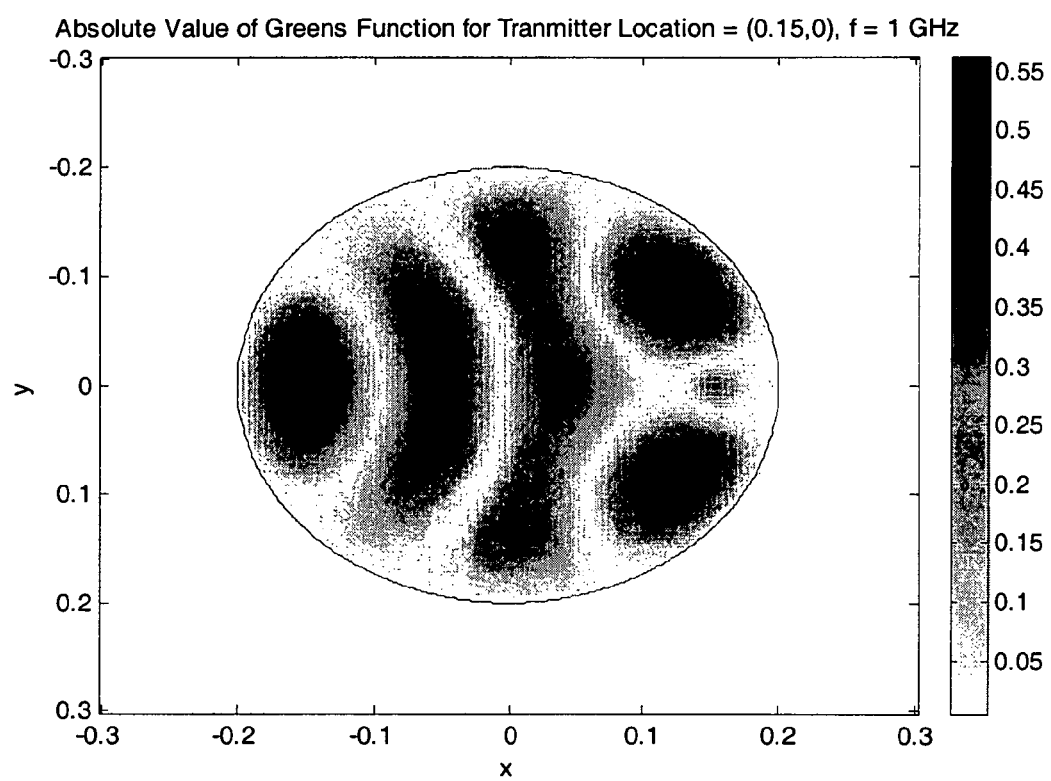
FIG. 2 graphically illustrates an embodiment of a Green's function according to the present invention.
Figure 2B:
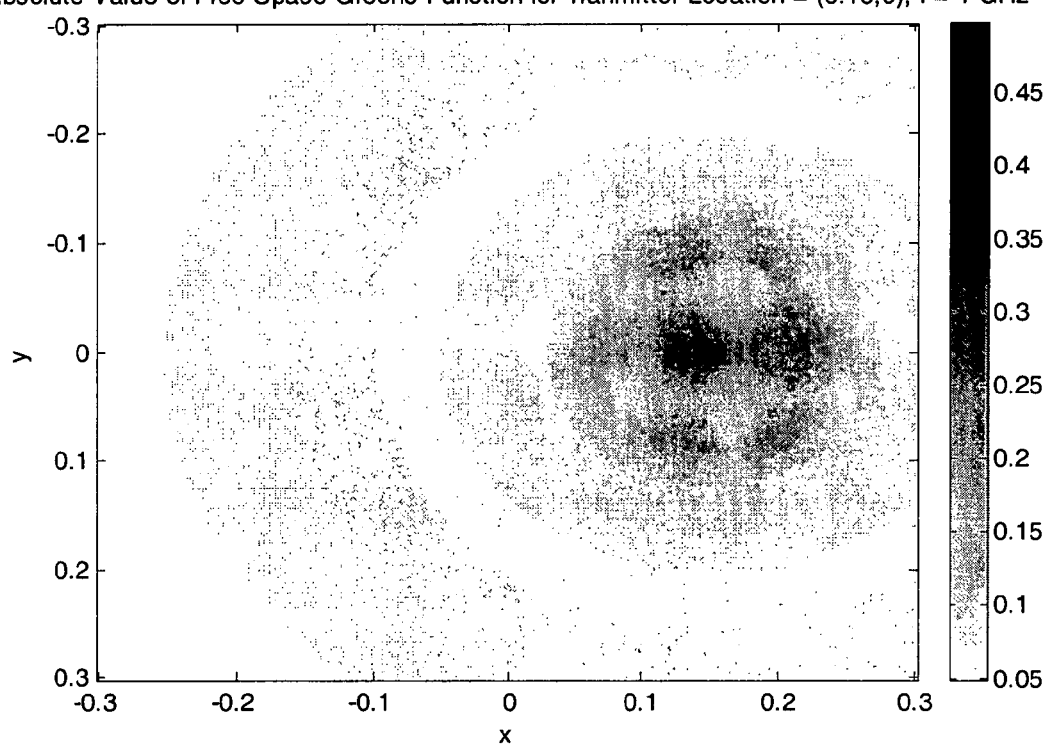

FIG. 2a shows a plot of the magnitude of Green's function for a frequency of 1 GHz inside a PEC cylinder of radius 20 cm with a lossless background, showing the field distortions produced by the conducting boundary. For comparison purposes, the regular free-space Green's function is plotted in FIG. 2b. Both Green's functions are singular at the source, but the discretization of the imaging region avoids these singularities. As shown in FIG. 2a, significantly more energy is located inside the PEC cylinder than for unbounded space of FIG. 2b.

In the context of computational electromagnetics, it is important to eliminate the surface integral in equation (25). The elimination of this integral allows for the application of standard (frequency domain) electromagnetic computational techniques, i.e., only a minimal change is required to switch an extant computational code to the new physical situation. In addition, the only singularity of the Green's function, $g(r, r')$, is located in the free-space term. This is due to the fact that the p term satisfies a homogenous differential equation. This means that current standard methods of extracting singularities in Method of Moments (MoM) codes remain unchanged—not a feature of other forms of the Green's function. To evaluate integrals of the function p, standard quadrature techniques are utilized because p is a smooth function. Thus, the derivation of the enclosed space scalar Green's function is completed.

The use of the modified Green's function in MR-CSI requires little or no changes at the conceptual level. However, the switch in Green's function does affect the numerical implementation. From a computational perspective, the most important aspects of the PEC Green's function are that the Green's function cannot be written in the form $g(r, r')=g(r-r')$ and the fields do not decay monotonically as the distance between r and r' increases. As these two properties are the core requirements required for the Fast Fourier Transform (FFT) and Fast Multiple (FM) acceleration methods respectively, the usual techniques used to make $O(N^2)$ (in memory and computational time) matrix operations into fast $O(N \log N)$ matrix operations are not applicable to matrices which result from the use of this Green's function. The lack of these two desirable properties is not formulation-dependent—they represent the actual physics of EM point sources in a PEC enclosed region. Hence, the existence of standing waves. Thus, re-formulating the Green function will not allow these acceleration methods to be applied. Therefore, for purposes of this embodiment of the application, all matrix multiplication is in the $O(N^2)$ format.

In practice, the infinite sum in equation (31) must be truncated. This is accomplished by taking enough terms in the series until it converges to within some error tolerance.

Several different synthetic data sets based on a 2D model have been generated to test the efficacy of the new microwave tomographic method. The incident field for every transmitter is a line-source which is parallel to the axis of the scatterer, in other words the incident field is taken to be the Green's function. The data is generated with a 2D Method of Moments (MoM) solver using pulse basis functions and point matching.

In order to test the inversion algorithm's performance in the presence of noise, 10% Root-Mean-Square (RMS) additive white noise is added to all scattered field measurements as follows:

$$f_k^{Noisy} = f_k^{meas} + \max(|f_k^{meas}|, \forall f_k^{meas}) \frac{N_s}{\sqrt{2}} (\alpha + j\beta), \quad (36)$$

where $\alpha$ and $\beta$ are uniformly distributed random numbers between −1 and 1, and $N_s$ is the desired fraction of noise—for purposes of this application $N_S$=0.1. For every inversion example, the conditions $Re(\chi)>0$ and $Im(\chi)<0$ are enforced at every step of the MR-CSI algorithm. For image clarity, all results illustrated in FIGS. 3, 4, and 5 display the negative of the imaginary part of the contrast, $-Im(\chi)=\epsilon''/\epsilon_b=\sigma/\omega$.

For the first numerical example, a simple scenario consisting of a square lossy scatterer is considered as shown in FIG. 3. The operating frequency is 1 GHz, and the scatterer is embedded in a PEC cylinder of radius 20 cm. The lossless background has a permittivity of $\epsilon_b=3\epsilon_0$ where $\epsilon_0$ is the permittivity of free space. The scatterer is illuminated by ten transmitters located evenly on a circle of radius 15 cm. The scattered field is measured at forty receiver points placed on a circle of radius 16 cm. The inversion region D is a square with edges of 20 cm length located in the centre of the PEC cylinder. The scatterer consists of a square object with sides of length 10 cm and a contrast of $\omega$=5.0−j4.0. Thus, the object has edges slightly larger than 1.3λ. The exact contrast is shown in FIG. 3a. The forward data were generated on a grid of 30×30 placed over D. In order to avoid an "inverse crime" as known to those skilled in the art, the inversion grid was selected to be 29×29 cells: this ensures that numerical quadrature points for the inverse and forward problem are distinct. The inversion results, or reconstruction from the bounded-space forward and inverse solvers, after 1024 iterations of the MR-CSI algorithm with the enclosed (PEC bounded) Green's function are shown in FIG. 3b.

The results do not illustrate a perfect reconstruction of the object. The overall shape of the scatterer is visible, however the magnitude of the real part of the contrast is not correct and the imaginary part of the contrast, while close to the exact values at the edges, does not reconstruct the interior of the object correctly. However, the it is critically important that the overall shape of the scatterer is visible.

For comparison purposes, new data is generated for the equivalent unbounded problem: all input parameters for the forward solver are kept the same, except the PEC cylinder is removed—the regular unbounded-space Green's function is used. Thus, the target is embedded in an infinite medium filled with the background permittivity of $\epsilon_b=3\epsilon_0$. The forward data are then inverted in the MR-CSI reconstruction using the regular unbounded-space Green's function.

Figure 3A:
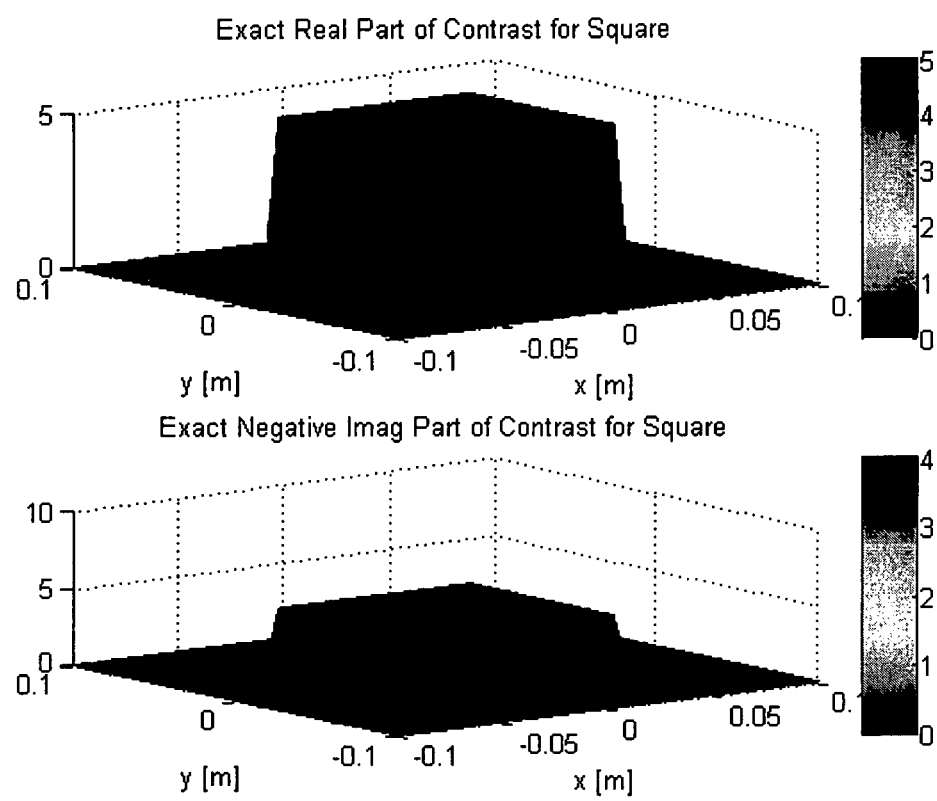
FIG. 3 graphically illustrates an embodiment of a square scatterer reconstruction according to the present invention.
Figure 3B:
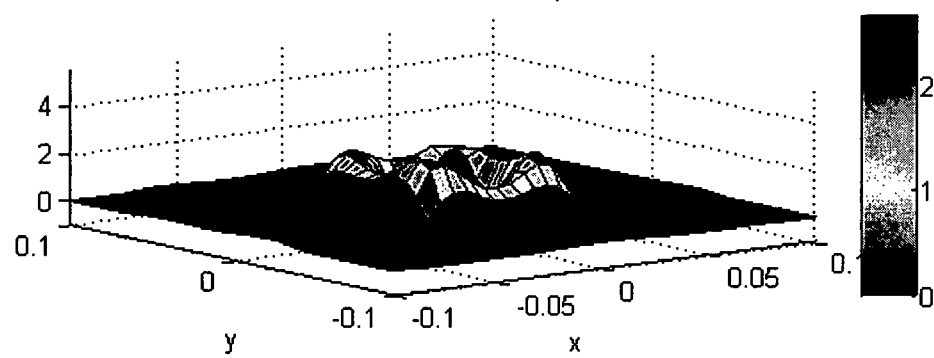
Figure 3B:
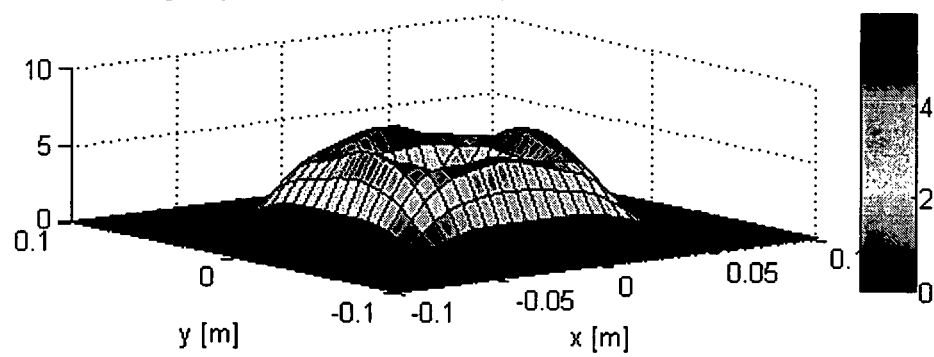
Figure 3C:
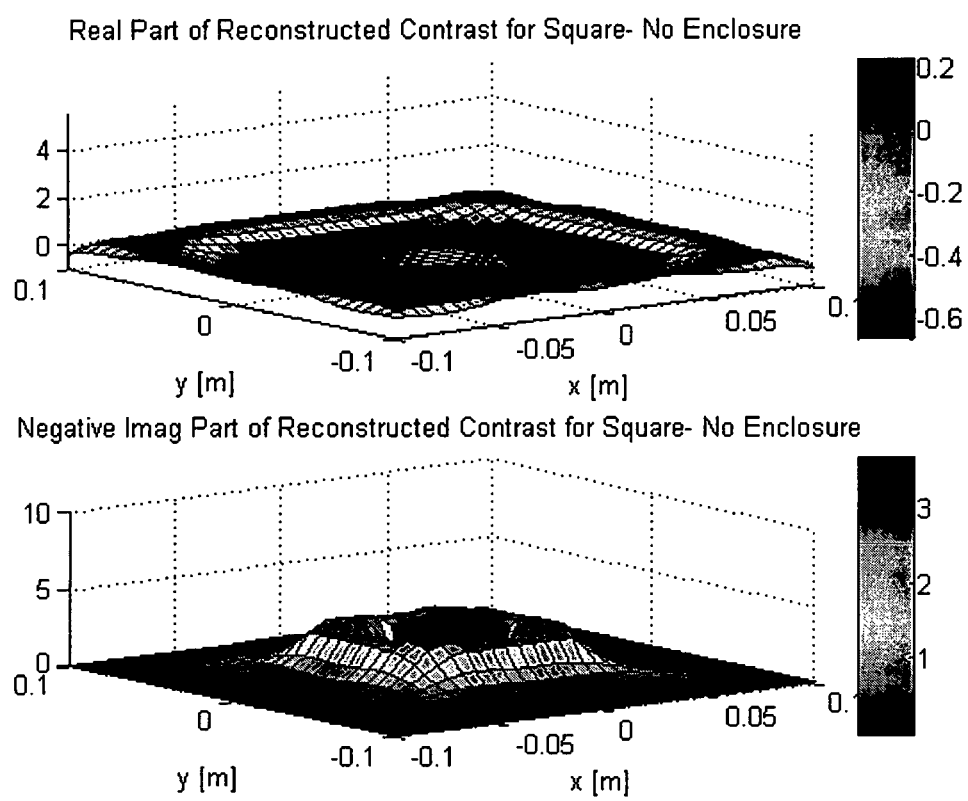

The reconstruction from the unbounded-space forward and inverse solvers is shown in FIG. 3c. For the real part of the contrast, not even the outline is visible. In fact, the reconstruction shows the contrast being negative, where it should be positive. The imaginary part of the reconstructed contrast shows the edges of the scatterer, but does not reach the exact level of 4.0.

In this case, it is clear that the use of the bounded-region tomographic system significantly improves the reconstruction. It is believed that the reconstruction is improved because more energy is located inside the lossy scatterer due to the bounding of the energy by the enclosure.

Next, the same scattering object used as a test case for the MR-CSI method is considered, as shown in FIG. 4. The scatterer consists of two low contrast concentric squares, with an inner square having sides of length h, with a contrast of x=0.6−j0.2, embedded in an exterior square having sides of 2λ and contrast $\chi$=0.3−j0.4. The exact contrast profile is shown in FIG. 4a. The imaging region D consists of a square having sides of length 3λ. A single frequency of 1 GHz is utilized, and free-space is assumed for the background. The forward data is generated on a grid of 31×31. Thirty transmitters are spaced evenly on a circle of radius 2.33λ=70 cm, and 40 receivers are placed evenly on a circle of radius 2.17λ=65 cm. The scatterer is surrounded by a PEC cylinder of radius 90 cm or approximately 3λ.

Figure 4A:
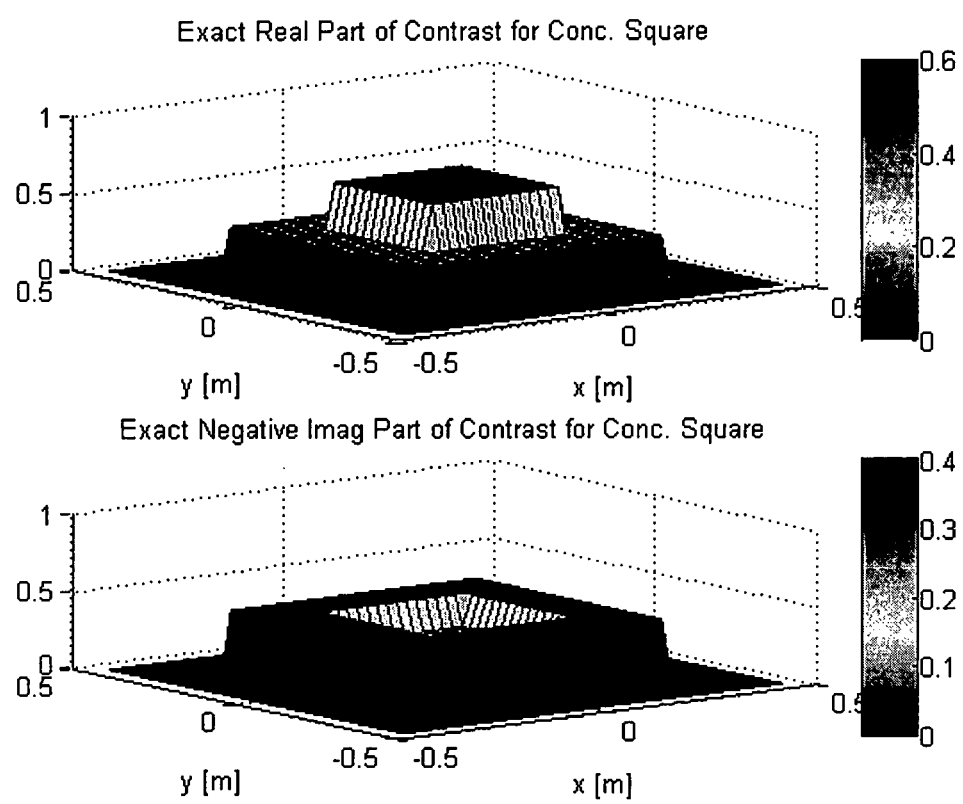
FIG. 4 graphically illustrates an embodiment of a low contrast concentric square scatter reconstruction according to the present invention.
Figure 4B:
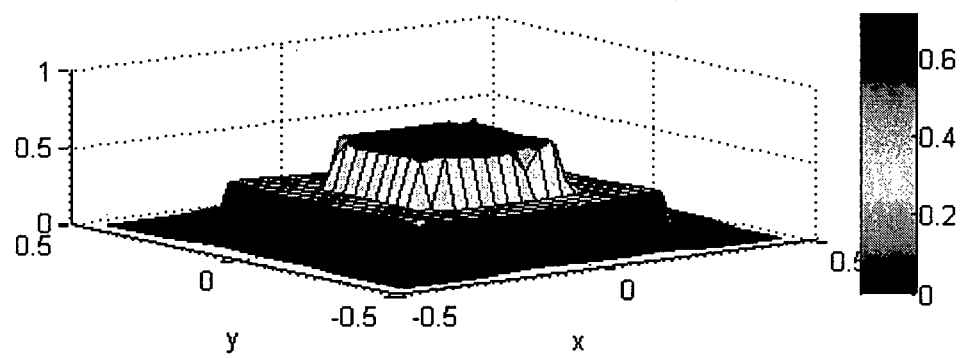
Figure 4B:
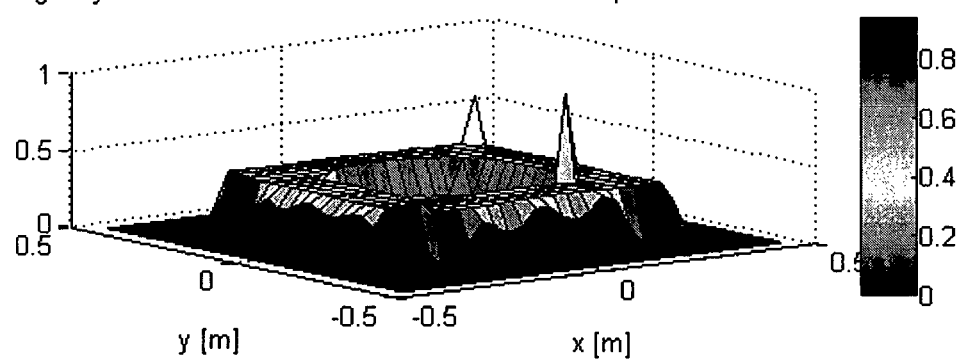

The data is inverted via the MR-CSI algorithm with the bounded Green's function. As before, the inversion mesh has 29×29 elements. The inversion results, or reconstruction from the bounded-space forward and inverse solvers, after 1024 iterations of the MR-CSI algorithm with the enclosed (PEC bounded) Green's function are shown in FIG. 4b. Although there are a few spurious pixels in the image, the two concentric squares are clearly visible.

Figure 4C:
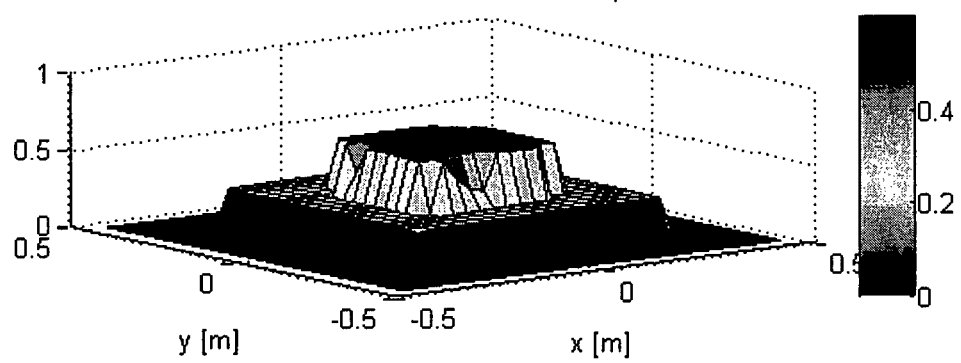
Figure 4C:
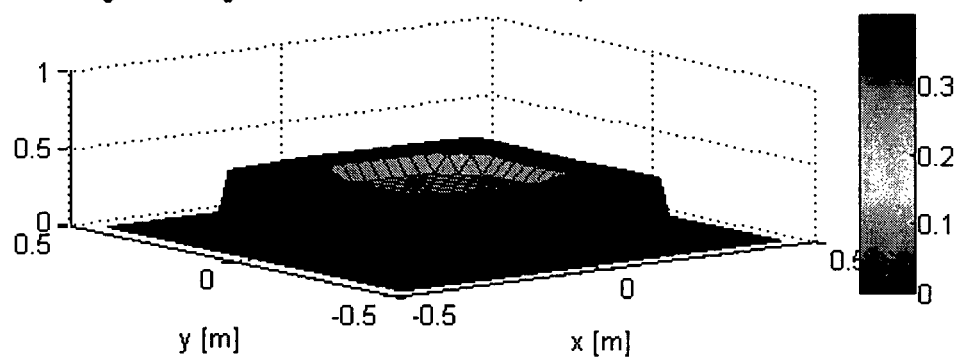

Again, the forward data is re-generated for the case where no PEC cylinder is present, but keeping every other parameter of the forward solver the same. The reconstruction from the unbounded-space forward and inverse solvers is shown in FIG. 4c. Unbounded free-space data is inverted via the MR-CSI algorithm with the unbounded Green's function. In this case, the results compare favorably with the reconstruction where the PEC cylinder is present because the contrast is lower than the previous case of the single square.

Figure 5A:
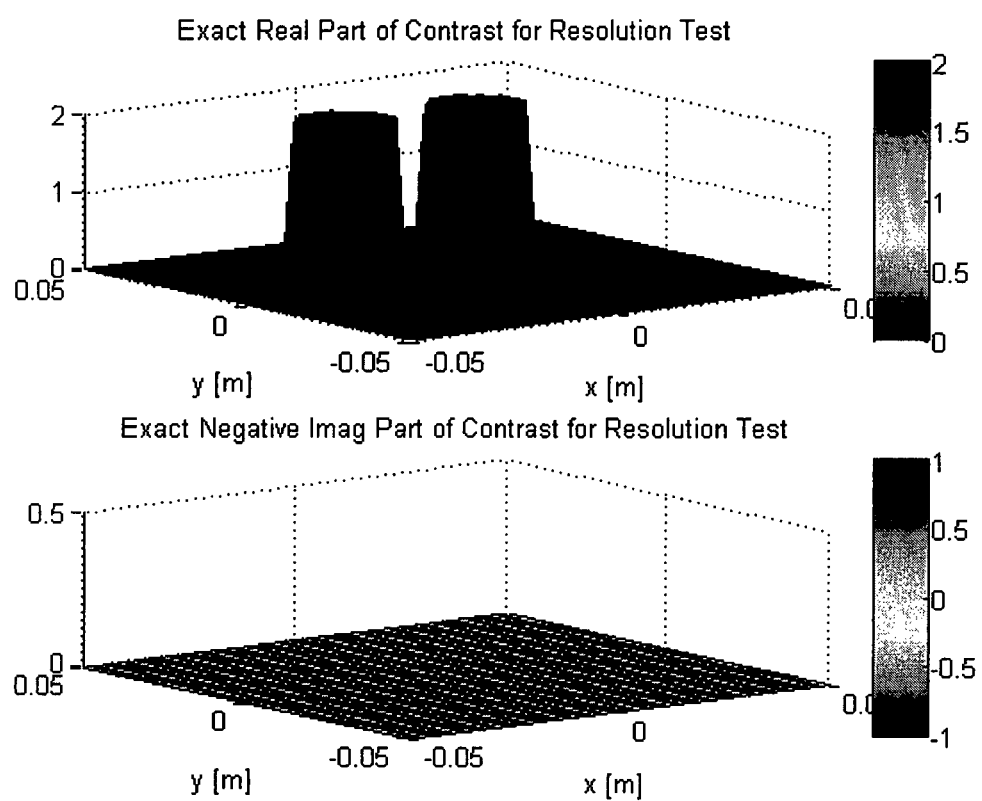
FIG. 5 graphically illustrates an embodiment of a two cylinder scatterer reconstruction according to the present invention.
Figure 5B:
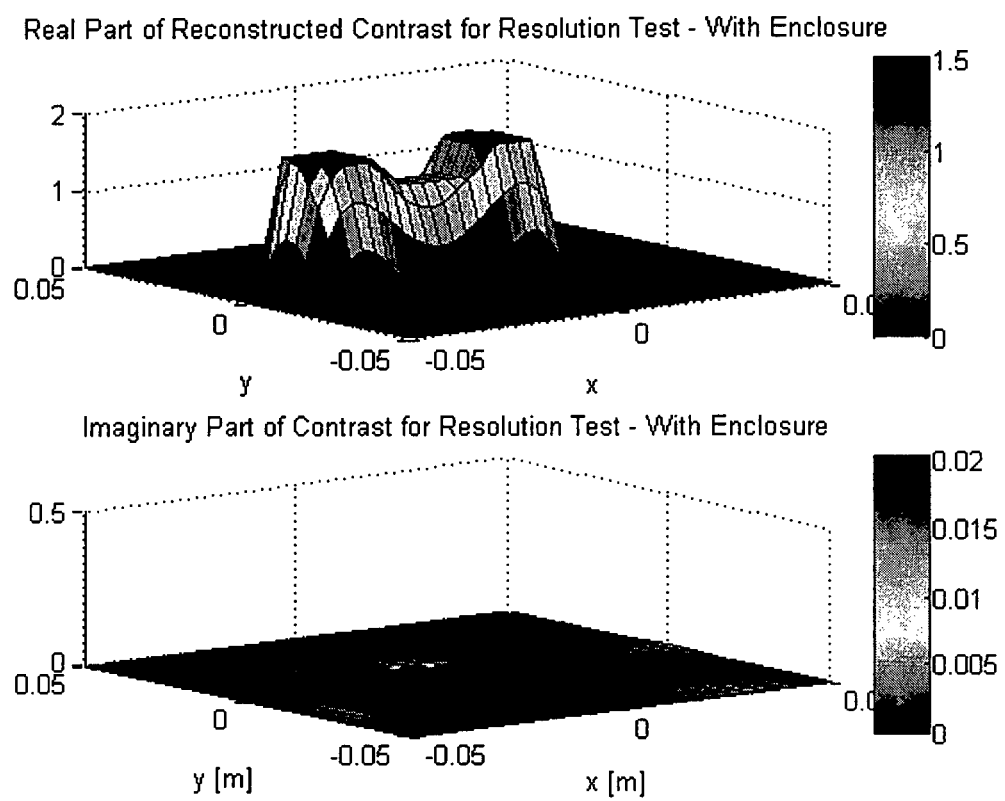
Figure 5C:
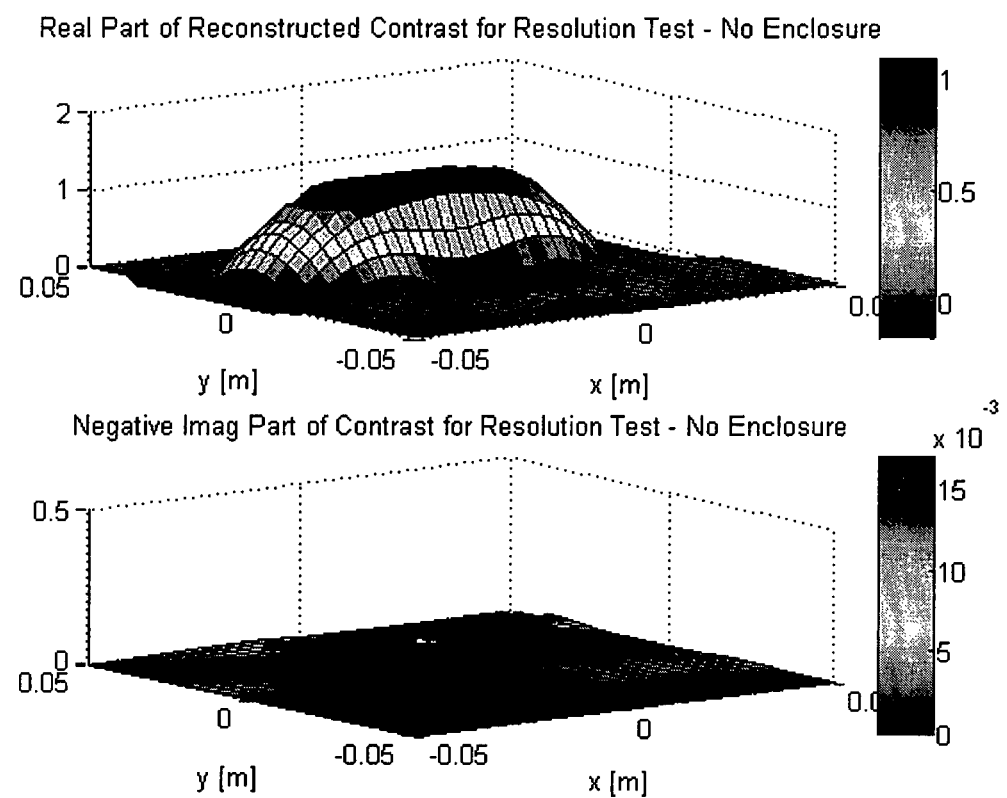

Next, a scatterer consisting of two high contrast cylinders is examined as shown in FIG. 5. Each cylinder has a radius of 1 cm and has a contrast of $\chi=2.0-j0.0$. The two cylinders are separated by 1 cm, and were illuminated by 10 transmitters at a frequency of 1.5 GHz. Thus, the separation between the two cylinders is $\frac{1}{20}^{th}$ of a wavelength. For the forward solver, the cylinders were discretized on a grid of 40×40 elements. The exact contrast profile is shown in FIG. 5a. Both the bounded Green's function and unbounded forward solvers were run, and the data are inverted via the appropriate MR-CSI program on a grid of 35×35 elements. The reconstruction from the bounded-space forward and inverse solvers, after 1024 iterations of the MR-CSI algorithm with the enclosed (PEC bounded) Green's function are shown in FIG. 5b and the reconstruction from the unbounded-space forward and inverse solvers is shown in FIG. 5c.

As shown in FIG. 5, the use of the enclosure significantly improves the reconstruction. In the case where the enclosure was utilized, the two cylinders are distinct. In the case where the enclosure was not utilized, the cylinders are completely blurred. Thus, the use of the enclosure has, in this case, given a higher resolution for these two scatterers.

Figure 6:
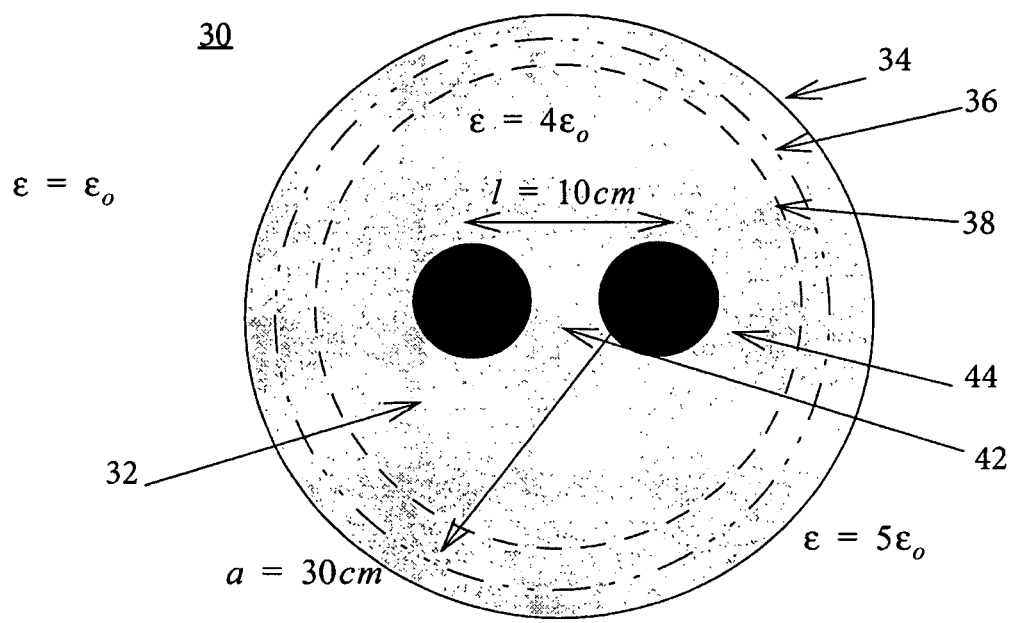
FIG. 6 illustrates an embodiment of a simulation of a tomographic imaging system according to the present invention.

When the unbounded domain Green's function is utilized in a lossless matching media MWT system, the artifacts introduced are quantified. FIG. 6 illustrates the simulation of a tomographic imaging system 30 without a PEC boundary. As shown in FIG. 6, the tomographic imaging system 30 has a cylindrical matching fluid 32 of $\epsilon=4$ $\epsilon_0$ of radius 30 cm. Inside the holding tank 34 are two cylindrical scatterers 42, 44 of radius 4 cm centered at (x, y)=(±5,0) cm and with permittivity of $\epsilon=5\epsilon_0$. Thirty transmitters are located on a circle 36 of radius 25 cm, and forty receivers are located on a circle 38 of radius 23 cm. An operation frequency of 1 GHz was utilized.

Figure 7A:
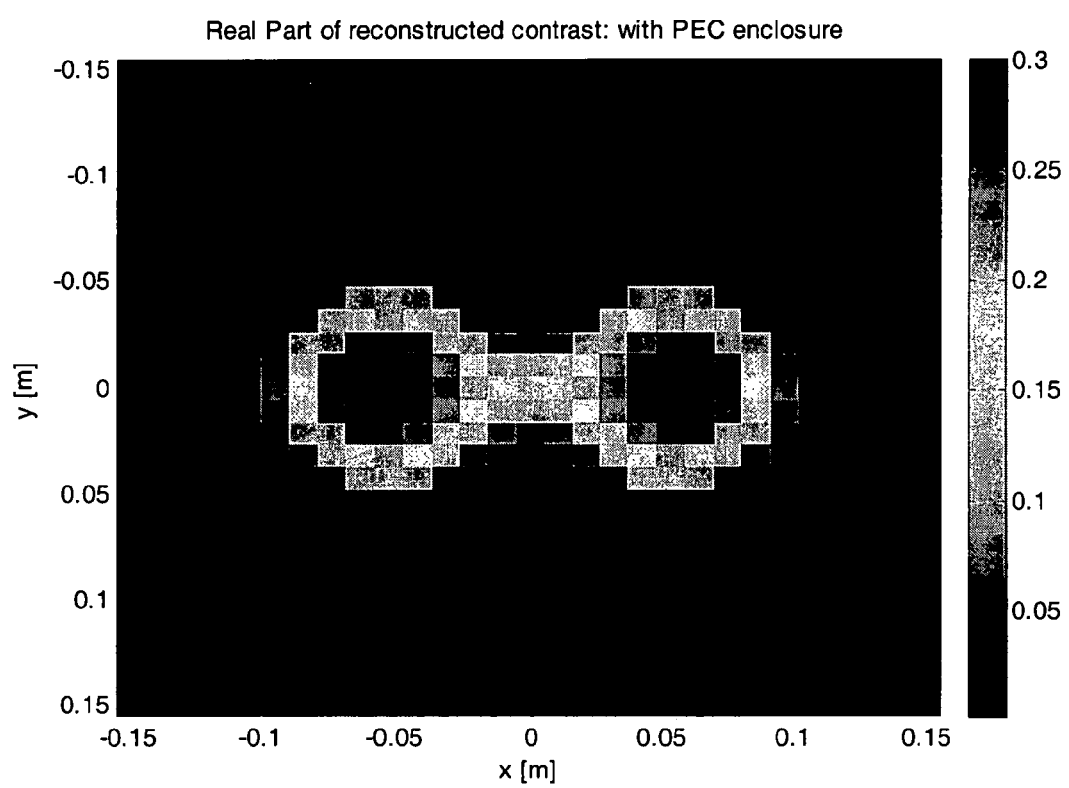
FIG. 7 graphically illustrates the results of the reconstruction of the simulated tomographic imaging system of FIG. 6.

Two computational experiments are performed. In the first, the embedding medium is located within a PEC cylinder. Data is generated, and inverted via the MR-CSI algorithm. The inversion results are shown in FIG. 7a illustrating that the two cylinders are reconstructed reasonably well.

Figure 7B:
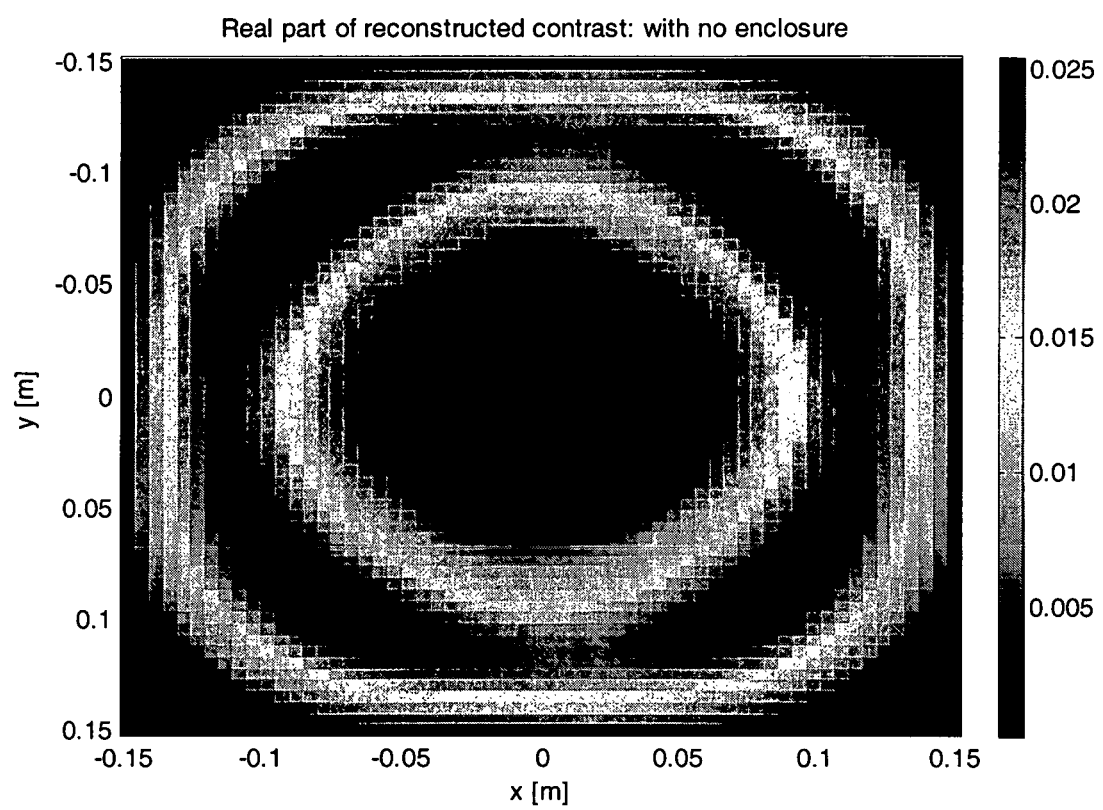

In the second computational experiment, synthetic data is generated taking into account the finite matching medium. In other words, an EM transparent tank is assumed that contains the matching medium. Data is generated, and inverted via the MR-CSI algorithm assuming that the inhomogeneities are embedded in an infinite background medium. Thus, the reflections from the edge of the embedding medium are not taken into account in the inversion, and will produce artifacts in the reconstruction. The reconstruction results are shown in FIG. 7b. As shown in FIG. 7b, this reconstruction is completely wrong since the reflections from the edge of the matching medium completely overwhelm the scattering from the two cylinders in the tank. Thus, the enclosed MWT system does not produce these artifacts. These inversion results improve with the use of a lossy matching medium, but as mentioned above, the tradeoff is adding undesirable loss to the scattering experiment.

As shown, for the case where the electrically conducting surface is a PEC cylinder, a version of the enclosed-domain Green's function is derived, which is amenable for use in existing computational solvers with only small modifications.

This Green's function was implemented in both a MoM forward solver for producing synthetic data and in the MR-CSI algorithm. The physical nature of the Green's function precludes the use of standard "fast" $O(N \log N)$ computational techniques, and currently all computations are implemented using algorithms with $O(N^2)$ computational complexity.

Several different synthetically generated examples are shown in which the use of a PEC cylinder to surround the scattering object improved the inversion results over the usual method of embedding the scatterer, in an infinite background medium. It is hypothesized that this is due to the fact that more energy is located inside the scatterer due to the reflections from the PEC surface. Another hypothesis is that the standing wave or resonant nature of the field distribution inside the enclosure contributes to the improved imaging. Yet another hypothesis is that the norm of the Green's function operator effects these improvements. It has already been shown in that the sufficient conditions for the convergence of both the distorted Born iterative method and Born iterative inversion methods are related to the norm of the Green's function operator.

The use of a tomographic imaging system with a finite matching medium and a reconstruction algorithm which does not take the finite nature of the matching fluid into account generates artifacts. The use of the external PEC cylinder in the tomographic system, combined with the use of the related Green's function in the inversion algorithm does not produce such artifacts.

Figure 8:
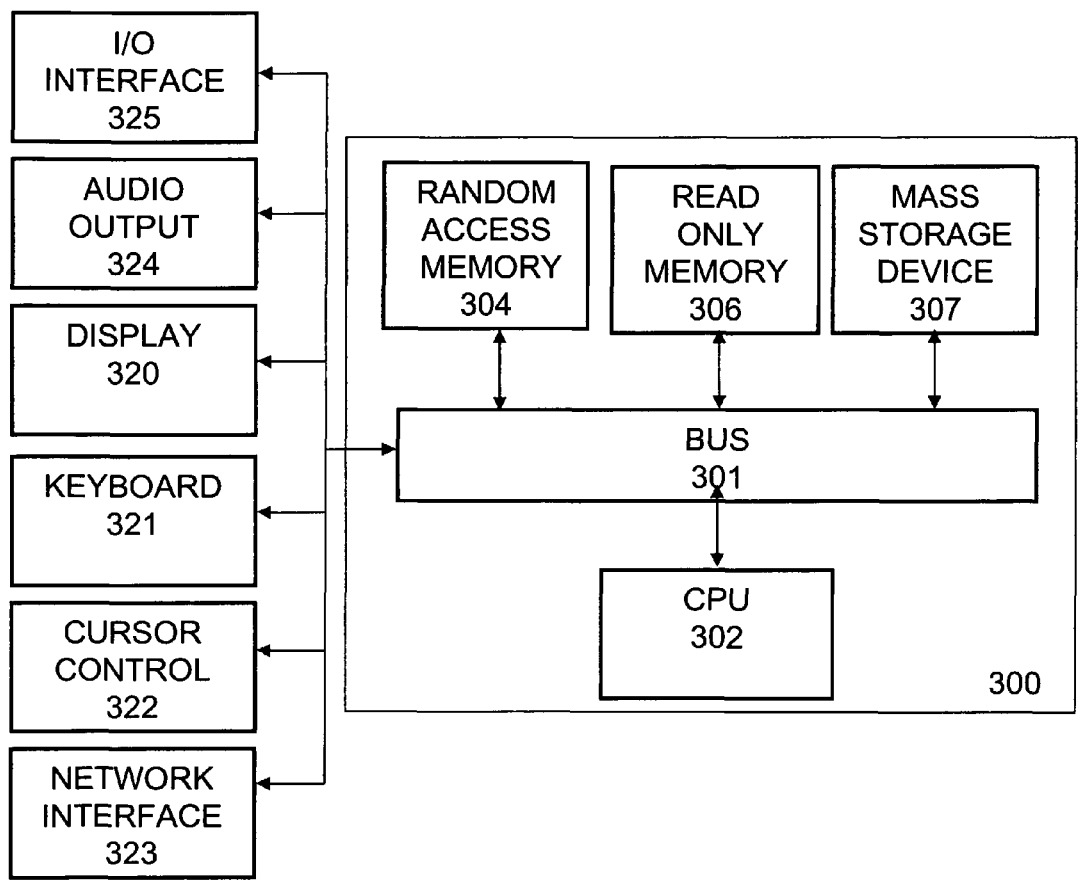
FIG. 8 is a block diagram of a general computer system according to the present invention.

FIG. 8 is a block diagram of a computer system 300 that implements the present invention. According to one embodiment of the present invention, the steps of improved tomography imaging, as well as other aspects of the present invention are implemented by a computer system 300. The processor or central processing unit (CPU) 302 in the system 300 may execute sequences of instructions stored in a memory. The memory may be a random access memory (RAM) 304, read-only memory (ROM) 306, a mass storage device 307, or any combination thereof. The CPU is coupled through a bus 301 to the memory. The mass storage device 307 could be a disk or tape drive for storing information such as data, algorithms and instructions. The information may be further stored within a database in the mass storage device 307. Information may be loaded into the memory of the computer from a storage device or from one or more other computer systems over a network connection.

The processor 302 includes a mathematical inversion technique and further comprises a plurality of components. A first computer processor component 302a defines an image region including an electrical conducting surface. Upon the application of radiation to the image region, a second computer processor component 302b gathers field distortion data. The field distortion data is reflected by the electrical conducting surface to produce an improved field distribution. A third computer processor component 302c accounts for the improved field distribution using the mathematical inversion technique, for example a Contrast Source Inversion (CSI)

algorithm or a Multiplicative-Regularized Contrast Source Inversion (MR-CSI) algorithm. The image region is reconstructed and illustrated on a display 320.

The display 320 is coupled to processor 302 through bus 301. The system 300 may further include a keyboard 321 for communicating information and command selections to processor 302. Another type of user input device may be a cursor control unit 322, which may be a device such as a mouse or trackball. Also coupled to processor 302 through bus 301 is an audio output port 324 for connection to speakers which output the audio content produced by computer system 300. Further coupled to processor 302 through bus 301 is an input/output (I/O) interface 325 which can be used to control and transfer information such as data to electronic devices connected to computer 300.

Network interface device 323 is coupled to bus 301 and provides a physical and logical connection between computer system 300 and the Internet. The architecture of FIG. 8 is provided only for purposes of illustration, and that the computer system 300 used in conjunction with the present invention is not limited to this specific architecture.

The separation of variables for the derivation of a PEC bounded Green's function is discussed below, including the eigenfunction expansion of equation (31), and the closed-form expressions for coefficients $A_n$ and $B_n$ of equation (34) and equation (35) respectively.

The 2D differential equation:

$$\nabla^2 p(r,r') + k^2 p(r,r') = 0 \; r \in V$$

$$p(r,r') = -g_{fs}(r,r) \; r \in S \qquad (37)$$

is solved where S is a circle of radius a. The cylindrical coordinates $r=(r,\theta)$ are introduced to write the Helmholtz equation in the cylindrical coordinates:

$$\frac{\partial^2 p}{\partial r^2} + \frac{1}{r}\frac{\partial p}{\partial r} + \frac{1}{r^2}\frac{\partial^2 p}{\partial \theta^2} + k^2 p = 0 \qquad (38)$$

$$0 < r < a, \; -\pi < \theta \leq \pi$$

$$p(a, \theta, r') = -g_{fs}(a, \theta, r')$$

Assuming that p may be written as:

$$p(r,\theta) = R(r)H(\theta), \qquad (39)$$

it is noted that:

$$\frac{R''}{R} + \frac{1}{r}\frac{R'}{R} + \frac{1}{r^2}\frac{H''}{H} + k^2 = 0, \qquad (40)$$

where prime and double prime denote first and second derivatives respectively. Due to the fact that R and H are independent, it is noted that:

$$r^2\frac{R''}{R} + r\frac{R'}{R} + r^2 k^2 = -\frac{H''}{H} = \alpha = \text{constant}, \qquad (41)$$

which results in two separated ordinary differential equations (ODE), solvable through the application of the boundary and periodicity conditions. The first ODE is given by:

$$H'' + \alpha H = 0, \qquad (42)$$

and the periodicity requirement gives the conditions:

$$H(-\pi) = H(\pi)$$

$$H'(-\pi) = H'(\pi) \qquad (43)$$

Equation (42) and equation (43) constitute a Sturm-Louiville system with eigenvalues:

$$\alpha = n^2 \qquad (44)$$

where n is a non-negative integer, with corresponding orthonormal eigenfunctions:

$$\frac{1}{\sqrt{2\pi}} \; n = 0, \quad \frac{1}{\sqrt{\pi}}\cos(n\theta) + \frac{1}{\sqrt{\pi}}\sin(n\theta) \; n > 0. \qquad (45)$$

The remaining differential equation is:

$$r^2 R'' + r R' + (r^2 k^2 - n^2) R = 0. \qquad (46)$$

Equation (46) is Bessel's equation of order n. The solution to this equation must be a summation of the Bessel functions of the form:

$$J_n(kr), Y_n(kr), H_n^{(1)}(kr), H_n^{(2)}(kr). \qquad (47)$$

where $J_n(kr)$ is the $n^{th}$ order Bessel function of the first kind, $Y_n(kr)$ is the $n^{th}$ order Bessel function of the second kind, and $H_n^{(1)}(kr)$ and $H_n^{(2)}(kr)$ are the $n^{th}$ order Hankel functions of the first and second kind, respectively. However, since the solution p is non-singular inside the PEC region, solutions to R must be of the form:

$$R_n(r) = J_n(kr), \qquad (48)$$

as $J_n(kr)$ is the only solution of Bessel's equation which is non-singular.

Thus, general solutions of the form $p(r,\theta;r') = R(r)H(\theta)$ may be now written as:

$$p(a, \theta, r') = \qquad (49)$$

$$\frac{A_0}{\sqrt{2\pi}} J_0(kr) + \sum_{n=1}^{\infty}\left(A_n J_n(kr)\frac{\cos(n\theta)}{\sqrt{\pi}} + B_n J_n(kr)\frac{\sin(n\theta)}{\sqrt{\pi}}\right),$$

where the coefficients, $A_0$, $A_n$ and $B_n$ are chosen to satisfy the boundary conditions, namely:

$$p(a,\theta,r') = -g_{fs}(a,\theta,r'), \qquad (50)$$

or:

$$p(a, \theta, r') = -g_{fs}(a, \theta, r') = \qquad (51)$$

$$\frac{A_0}{\sqrt{2\pi}} J_0(ka) + \sum_{n=1}^{\infty}\left(A_n J_n(ka)\frac{\cos(n\theta)}{\sqrt{\pi}} + B_n J_n(ka)\frac{\sin(n\theta)}{\sqrt{\pi}}\right).$$

Making use of the orthonormal nature of the eigenfunctions of $H(\theta)$, both sides of equation (51) are multiplied by $1/\sqrt{2\pi}$, and integrate from $\theta = -\pi$ to $\theta = \pi$:

$$\frac{-1}{\sqrt{2\pi}}\int_{-\pi}^{\pi} g_{fs}(a, \theta, r')d\theta = \qquad (52)$$

$$A_0 J_0(ka) \; \text{or} \; A_0 = \frac{-1}{\sqrt{2\pi} J_0(ka)}\int_{-\pi}^{\pi} g_{fs}(a, \theta, r')d\theta.$$

To determine $A_n$, both sides of equation (51) are multiplied by $\cos(m\theta)/\sqrt{\pi}$, and integrate over $\theta$, which results in:

$$A_n = \frac{-1}{\sqrt{\pi}\, J_n(ka)} \int_{-\pi}^{\pi} g_{fs}(a, \theta, r')\cos(n\theta)d\theta. \qquad (53)$$

and by similar argument:

$$B_n = \frac{-1}{\sqrt{\pi}\, J_n(ka)} \int_{-\pi}^{\pi} g_{fs}(a, \theta, r')\sin(n\theta)d\theta. \qquad (54)$$

These two integrals may be derived in closed form by considering the identity:

$$H_0^{(2)}(k|r-r'|) = \begin{cases} \sum_{m=-\infty}^{\infty} J_m(kr) H_m^{(2)}(kr') e^{jm(\theta-\theta')} & r \leq r' \\ \sum_{m=-\infty}^{\infty} J_m(kr') H_m^{(2)}(kr) e^{jm(\theta-\theta')} & r \geq r' \end{cases}, \qquad (55)$$

where r, r' and θ, θ' are the cylindrical coordinates for r and r' respectively. For the integrals in equation (53) and equation (54), r>r', thus:

$$A_n = \frac{-1}{4j\sqrt{\pi}\, J_n(ka)} \int_{-\pi}^{\pi}\left(\sum_{m=-\infty}^{\infty} J_m(kr') H_m^{(2)}(kr) e^{jm(\theta-\theta')}\right)\cos(n\theta)d\theta, \qquad (56)$$

which equals:

$$A_n = \frac{-1}{4j\sqrt{\pi}\, J_n(ka)} \left(\sum_{m=-\infty}^{\infty} J_m(kr') H_m^{(2)}(kr) e^{-jm\theta'}\right)\int_{-\pi}^{\pi} e^{jm\theta}\cos(n\theta)d\theta, \qquad (57)$$

and since:

$$\int_{-\pi}^{\pi} e^{jm\theta}\cos(n\theta)d\theta = \begin{cases} \pi & \text{if } |n| = m \\ 0 & \text{otherwise} \end{cases} \qquad (58)$$

$A_n$, is equal to the expression given in equation (34). The derivation for $B_n$, proceeds in an analogous manner.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method for an improved tomographic imaging system, comprising,
   inputting information through a user interface, wherein the information defines an image region;
   creating an electrical conducting surface surrounding the entire image region according to a first instruction executed by a processor;
   applying radiation to the image region according to a second instruction executed by the processor to measure only field distortions reflected by the electrical conducting surface surrounding the entire image region;
   producing by the processor an improved field distribution from the field distortions;
   utilizing by the processor a mathematical inversion technique that accounts for the improved field distribution to reconstruct the image region to obtain a reconstructed image region; and
   illustrating the reconstructed image region on a display device.

2. The method of claim 1 wherein the mathematical inversion technique includes a Green's function.

3. The method of claim 1 wherein the electrical conducting surface is modeled as a Perfect Electric Conductor (PEC).

4. The method of claim 3 wherein the Perfect Electric Conductor (PEC) is in the shape of a circular cylinder.

5. The method of claim 1 wherein the mathematical inversion technique is a Contrast Source Inversion (CSI) algorithm.

6. The method of claim 5 wherein the Contrast Source Inversion (CSI) algorithm is a Multiplicative-Regularized Contrast Source Inversion (MR-CSI) algorithm.

7. An improved tomographic imaging system, comprising:
   a user interface configured to receive information that defines an image region;
   a computer processor including a plurality of processor components, the plurality of processor components comprising:
      a first computer processor component that executes a first instruction to create an electrical conducting surface that surrounds the entire image region, wherein radiation is applied to the image region and reflected by the electrical conducting surface;
      a second computer processor component that executes a second instruction to gather only field distortion data measured by the radiation reflected by the electrical conducting surface to produce an improved field distribution;
      a third computer processor component that executes a third instruction to utilize a mathematical inversion technique that includes a Green's function to account for the improved field distribution to obtain a reconstructed image region; and
   a display to illustrate the reconstructed image region.

8. The system of claim 7 wherein the mathematical inversion technique is a Contrast Source Inversion (CSI) algorithm.

9. The system of claim 7 wherein the mathematical inversion technique is a Multiplicative-Regularized Contrast Source Inversion (MR-CSI) algorithm.

* * * * *